US005556408A

United States Patent [19]
Farhat

[11] Patent Number: 5,556,408
[45] Date of Patent: Sep. 17, 1996

[54] EXPANDABLE AND COMPRESSIBLE ATHERECTOMY CUTTER

[75] Inventor: Lawrence Farhat, Carlsbad, Calif.

[73] Assignee: Interventional Technologies Inc., San Diego, Calif.

[21] Appl. No.: 429,939

[22] Filed: Apr. 27, 1995

[51] Int. Cl.$^6$ .......................... A61B 17/14; A61B 17/22
[52] U.S. Cl. ........................................ 606/180; 606/159
[58] Field of Search ..................................... 606/180, 159

[56] References Cited

U.S. PATENT DOCUMENTS 4,966,604  10/1990  Reiss ........................................ 606/159
5,395,311   3/1995  Andrews .................................. 606/159

Primary Examiner—Michael Powell Buiz
Assistant Examiner—Kevin Truong
Attorney, Agent, or Firm—Nydegger & Associates

[57] ABSTRACT

An expandable and compressible atherectomy cutter for cutting plaque from a stenosis includes a distal hub and a proximal hub joined by a plurality of resilient blades. The blades are shaped to describe a cutting radius which may be compressed to allow the cutter to be inserted into a guide catheter during insertion and removal of the cutter from the patient. The proximal hub is attached to the distal end of a torque tube. A conically-shaped, flexible funnel extends distally from the distal end of the torque tube with the resilient blades located partially within the funnel. In use, the cutter is rotated and advanced to clear a stenosis in a vessel of a patient. At the same time, fluid is withdrawn from the torque tube causing debris to be gathered through the funnel and removed from the patient. Debris removal is enhanced by the channeling effect of the funnel.

17 Claims, 2 Drawing Sheets

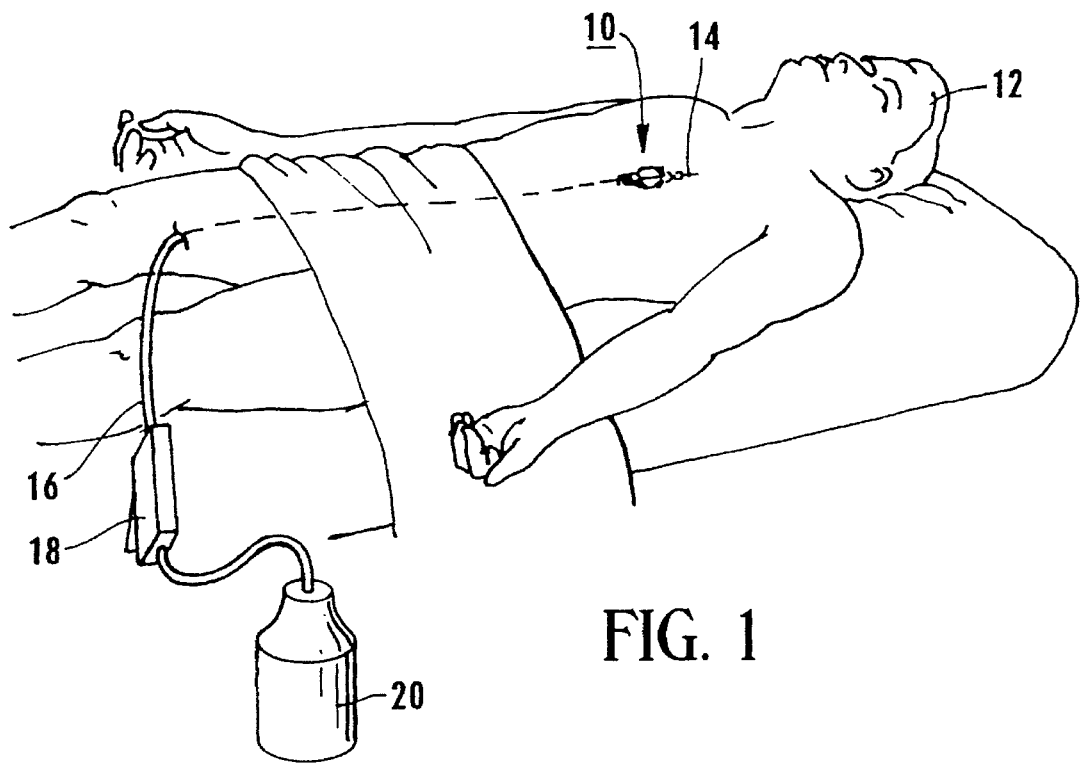
FIG. 1
FIG. 2
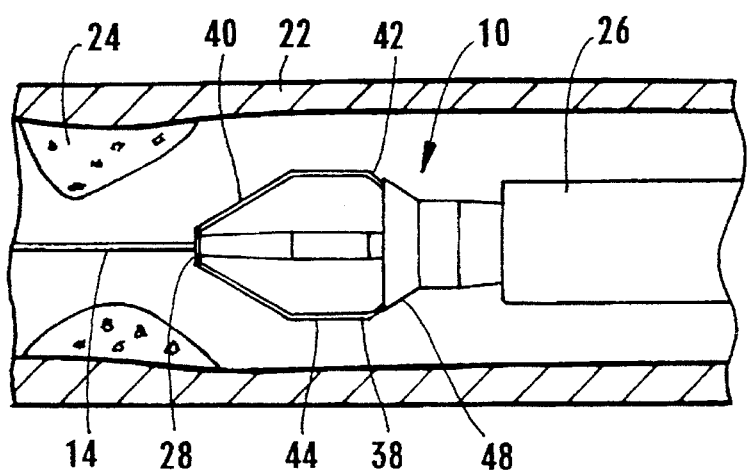

EXPANDABLE AND COMPRESSIBLE ATHERECTOMY CUTTER

FIELD OF INVENTION

The present invention pertains generally to medical devices which are useful for removing a stenotic segment from the artery of a patient. More particularly, the present invention pertains to atherectomy devices which use a cutting element to remove plaque from an artery. The present invention is particularly, but not exclusively, useful as an atherectomy cutter which has expandable/compressible blades for varying the cutting radius of the device.

BACKGROUND OF THE INVENTION

It is well known that any significant reduction or restriction in the flow of blood through the arteries of the body can cause complications which may have serious consequences. As a result, it is extremely important for the health of the patient that a stenosis, or blockage, which is causing such a condition be eliminated. One well known and frequently used procedure to accomplish this task is popularly known as angioplasty. For a basic angioplasty procedure, a dilatation balloon is positioned in the arterial lumen at the stenosis and the balloon is inflated to open the artery by dilating the plaque-restricted lumen at the stenosis. With angioplasty procedures, however, the plaque, remains in the artery and is not removed. Unfortunately, in some cases, it appears that the plaque which is left behind in the artery may cause a re-stenosis in the artery.

As an alternative to angioplasty, atherectomy procedures have been developed to resolve the problems caused by blocked arteries. However, unlike an angioplasty procedure, the atherectomy procedure mechanically cuts and then removes the plaque which is creating the stenosis from the artery. The cutting devices which are used for this task must, of necessity, be rather small. They must also have sufficient structural strength to cut the plaque in performance of the atherectomy procedure. Additionally, they must be operationally reliable. Many examples of such cutting devices can be given. For instance, U.S. Pat. No. 4,895,166 which issued to Farr et al. for an invention entitled "Rotatable Cutter for the Lumen of a Blood Vessel" and which is assigned to the same assignee as the present invention, discloses a cone-shaped cutter which may be rotatably advanced through a vessel to remove stenotic material. Alternatively, U.S. Pat. No. 4,589,412 which issued to Kensey for an invention entitled "Method and Apparatus for Surgically Removing Remote Deposits" discloses a triangular rotatable cutter which cuts stenotic material as it is rotatably advanced through a vessel.

One problem which must be confronted in any procedure, whether it be an angioplasty or an atherectomy procedure, is the size of the entry site which can be used for introducing the medical device being used into the artery. Standard practices accept an entry site which has a diameter of only approximately twelve French, or approximately four millimeters. Thus, any device which is to be positioned in the artery must pass through a guide catheter whose outer diameter is not larger than twelve French. The inner diameter of such an introducer is generally, however, on the order of only nine French. The consequence is that any device which is effectively insertable into the artery of a patient must be capable of assuming a configuration wherein the greatest dimension across the device is no more than approximately nine French. It happens, however, that to properly clear a stenotic segment it is sometimes necessary to create a lumen through the stenotic segment which has a greater diameter than nine French. To do this by an atherectomy procedure, the cutter being used must be capable of expanding beyond the nine French restriction imposed at the entry site.

Several examples of expandable cutting devices which are specifically useful as medical devices for atherectomy procedures can be given. For instance, U.S. Pat. No. 4,966,604 which issued to Reiss for an invention entitled "Expandable Atherectomy Cutter with Flexibly Bowed Blades" and is assigned to the same assignee as the present invention, discloses a rotatable atherectomy cutter whose flexible blades may be bowed outward to give the cutter a variable cutting radius. Alternatively, U.S. Pat. No. 4,986,807 which issued to Farr for an invention entitled "Atherectomy Cutter with Radially Projecting Blade" and is also assigned to the same assignee as the present invention, discloses a rotatable cutter featuring a single blade which may be selectively extended thereby increasing the cutting radius of the cutter. There is, of course, still a need for other expandable atherectomy cutters which can meet the specific needs of a specifically desired protocol.

Another problem which must be confronted in an atherectomy procedure is the existence of loose plaque which is necessarily generated as the stenotic segment is cut. It may be appreciated that failure to remove plaque of this type may adversely effect the health of the patient involved. In some cases, these adverse effects may be severe. As a result, atherectomy devices generally employ some means whereby loose plaque may be removed from the patient as the stenosis is cut. To this end, many atherectomy devices include means that allows fluid to be forcefully removed from the cutting site. As the fluid is removed, plaque fragments cut from the stenotic segment are carried with the fluid and removed from the patient. Practice has shown that removal of fluid from the cutting site is generally an effective technique for reducing the quantity of loose plaque within a vessel undergoing an atherectomy procedure. It is still the case, however, that loose stenotic material may remain in the vessel after completion of the atherectomy procedure. This is particularly true in cases where advancement of the atherectomy device within the vessel causes the cutter to move past cut plaque before it is removed from the vessel. As a result, it is clear that improved methods for removing loose plaque are generally desirable.

Another problem which must be confronted in an atherectomy procedure involves the wide variation in locations in which stenotic segments may occur. Specifically, it happens that atherectomy procedures can be performed in the coronary arteries, the carotid arteries, the renal arteries, and in the peripheral arteries. Each set of arteries is different and presents different challenges to the atherectomy procedure. As a result, there is the need to provide a generalized technology for atherectomy devices which may be easily adapted to the needs of varying atherectomy procedures in varying locations.

In light of the above, it is an object of the present invention to provide a compressible/expandable atherectomy cutter which features a small diameter compressed configuration and a large diameter expanded configuration. Still another object of the present invention is to provide a compressible/expandable atherectomy cutter which includes an enhanced ability to remove loose stenotic material from the cutting site. Yet another object of the present invention is to provide a compressible/expandable atherectomy cutter which reduces the probability that loose stenotic material will pass the advancing cutter before such material may be removed. Still another object of the present invention is to provide a compressible/expandable atherectomy cutter which whose basic design may be easily adapted to suit the needs of different atherectomy procedures. Yet another object of the present invention is to provide a compressible/ expandable atherectomy cutter which is relatively simple to use, relatively easy to manufacture, and comparatively cost effective.

SUMMARY OF THE INVENTION

For the present invention, an expandable and compressible atherectomy cutter includes a distal hub and a proximal hub. The distal hub and the proximal hub are each formed with an aperture. Additionally, the distal hub and the proximal hub are aligned with each other to define an axis of rotation and the distal hub and the proximal hub are separated by a predetermined distance on the axis of rotation.

The atherectomy cutter also includes a plurality of cutting blades. Each blade is formed as a flat strip with a proximal end and a distal end. Between the distal end and proximal end, each blade has a central section. The distal end of each blade is connected to the distal hub. In a similar fashion, the proximal end of each blade is connected to the proximal hub. The blades are constructed of a resilient, bendable material and each blade is formed with a predetermined configuration. The predetermined configuration causes the central section of each blade to arch radially away from the longitudinal axis of the cutter. Together, the plurality of blades describe a cutting radius. It may be appreciated that different embodiments of the present invention may describe varying cutting radii. However, practice has demonstrated that a cutting radius of twelve french, or four millimeters, is particularly effective.

A torque tube is connected to the proximal hub of the cutter so that rotation of the tube causes an equivalent rotation of the cutter around the axis of rotation. The lumen of the torque tube is attached in fluid communication with the aperture formed in the proximal hub allowing fluid and debris to be withdrawn from the area around the cutter through the torque tube. A conically-shaped tubular funnel is attached to the torque tube. More specifically, the funnel is formed with an interior surface and attached with the base of the funnel positioned around the torque tube at the connection between the torque tube and the proximal hub. The funnel extends distally from the torque tube and expands radially. The lumen of the torque tube is connected in fluid communication with the funnel and the proximal ends of the blades are positioned within the interior surface of the funnel. The funnel provides a guiding effect which directs fluid and debris into the aperture of the proximal hub as fluid is withdrawn from the lumen of the torque tube. Additionally, the funnel reduces the amount of debris which passes, or slips by, the cutter as the cutter advances and before the debris may be withdrawn. The funnel is preferably fabricated from a flexible polymeric material such as PET.

Operationally, the cutter is first inserted into a tubular guide catheter. The guide catheter has an outside diameter that will generally be less than four millimeters and an internal diameter that will generally not exceed three millimeters. It may be appreciated that the cutting radius of the cutter exceeds the internal diameter of the guide catheter. As a result, as the cutter is inserted into the guide catheter, a compressing force is applied to the cutting blades of the cutter. The compressing force causes the arched configuration of the blades to temporarily flatten. As a result, the predetermined separation between the proximal hub and the distal hub increases. As the cutter is inserted into the guide catheter, the flexible material of the funnel allows the funnel to be temporarily compressed thereby allowing the funnel to fit within the lumen of the guide catheter.

After the cutter is inserted into the guide catheter, a guide wire is inserted into the artery of a patient. More specifically, the distal end of the guide wire is inserted into the artery of the patient and advanced until it has passed the stenosis that is the target of the procedure. The proximal end of the guide wire is then threaded through the aperture of the distal hub and the aperture of the proximal hub and passed through the torque tube. The cutter, which is still enclosed in the guide catheter, may then be inserted into the artery of the patient and advanced until it has nearly reached the target stenosis.

Once the cutter and guide catheter have been correctly positioned, the cutter is advanced out of the guide catheter. As the cutter advances, the compressing force that had confined the blades of the cutter is removed allowing the blades to reassume their original cutting radius. At the same time, the flexible material of the funnel allows the funnel to expand. Torque may then be applied to the torque tube causing the cutter to rotate. The rotating cutter is then advanced into the target stenosis.

As the rotating cutter advances into the stenosis, a vacuum source connected to the torque tube creates a low pressure condition within the torque tube. The low pressure condition within the torque tube causes fluid to flow through the funnel and into the lumen of the torque tube. The fluid flow causes loose stenotic material and other debris to be withdrawn from the vessel. Additionally, the funnel acts as a partial seal and reduces the natural tendency for debris to pass the cutter as the cutter advances through the vessel.

Once the target stenosis has been removed, the cutter may be advanced to treat other targets. Alternatively, the cutter may be withdrawn into the guide catheter and the cutter and catheter may be withdrawn to complete the procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of the expandable/compressible cutter of the present invention shown in its operational environment;

FIG. 2 is a cross-sectional view of an artery in a patient having a stenotic segment in the artery with the cutter of the present invention operationally positioned in the artery;

DESCRIPTION OF PREFERRED EMBODIMENTS

Figure 3:
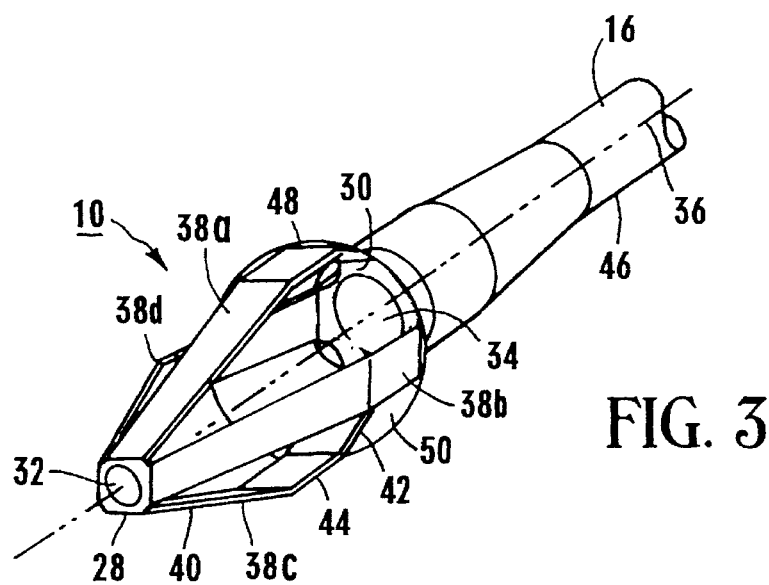
FIG. 3 is an isometric view of an embodiment of the expandable/compressible cutter of the present invention.

An expandable/compressible atherectomy cutter in accordance with the present invention is shown in FIG. 1 in its operational environment and is generally designated 10. As shown, the cutter 10 has been inserted into an artery of the patient 12 and positioned in the artery for the purpose of removing plaque from a stenosis in the artery. In order to properly position the cutter 10 in the artery, it is inserted over a previously positioned guide wire 14. Once the cutter 10 is properly positioned against a stenotic segment in an artery of the patient 12, the cutter 10 is rotated by the rotatable torque tube 16 to cut plaque from the stenosis. Rotation of the cutter 10 is controlled by the control unit 18. Additionally, control unit 18 also controls the operation of a vacuum source 20 which creates suction through the torque tube 16 to remove cut plaque from the artery of the patient.

The actual operational environment for the cutter 10 is, perhaps, best appreciated by reference to FIG. 2. There it will be seen that the cutter 10 is positioned in an artery 22 against an accumulation of plaque, or stenosis 24. FIG. 2 also shows that cutter 10 is intended to be used in combination with a guide catheter 26. More specifically, it may be appreciated that cutter 10 is intended to be positioned within guide catheter 26 both during insertion and withdrawal of cutter 10 from the artery 22. As indicated previously, conventional protocols limit the outside diameter of the guide catheter 26 to approximately twelve French (four millimeters) or less. As a result, the guide catheter 26 will have an inside diameter that will generally not exceed nine French (three millimeters). Thus, cutter 10 must be compressible to a configuration having a dimension less than nine French to be positioned within guide catheter 26.

The structure that allows cutter 10 to be positioned within guide catheter 26 is best seen in FIG. 3. As seen in FIG. 3, cutter 10 includes a distal hub 28 and a proximal hub 30. The distal hub 28 is formed with an aperture 32. Similarly, the proximal hub 30 is formed with an aperture 34. The distal hub 28 and the proximal hub 30 are aligned with each other to define an axis of rotation 36.

A plurality of resilient blades 38a, 38b, 38c and 38d join the distal hub 28 and the proximal hub 30. Each of the blades, such as blade 38a includes a distal end 40 and a proximal end 42. Between the distal end 40 and the proximal end 42, each blade 38a–38d includes a central section 44 which is generally parallel to the axis of rotation 36. As shown in FIG. 3, the distal end 40 of each blade 38a–38d is joined to the distal hub 28 and projects radially outward and proximally from the distal hub 28. In a like fashion, the proximal end 42 of each blade 38a–38d is connected to the proximal hub 30 and projects radially outward and distally from the proximal hub 30. Between the distal end 40 and proximal end 42, the central section 44 of each blade 38a–38d is held at a predetermined radial distance from the axis of rotation. For the purposes of the present invention, the blades 38a–38d are preferably formed from panels or strips of resilient material. In general, many materials may be used to form the blades 38a–38d of the present invention. Practice has demonstrated, however, that certain resilient metals, including stainless steels, are particularly suitable. Continuing with FIG. 3, it may be seen that torque tube includes a distal end 46 and the proximal hub 30 is connected to the distal end 46 so that rotation of the torque tube 16 causes an equivalent rotation of the cutter 10 around the axis of rotation 36. Additionally, the lumen of the torque tube 16 is attached in fluid communication with the aperture 34 formed in the proximal hub 30. A conically-shaped tubular funnel 48 is attached at the distal end 46 of the torque tube 16. The funnel 48 is formed with a interior surface 50 and extends distally from the distal end 46 of the torque tube 16 and expands radially away from the axis of rotation 36.

The position of the funnel 48 locates the proximal end 42 of each of the blades 38a–38d within the interior surface 50 of the funnel 46. Together, the funnel 48, aperture 34 formed in the proximal hub 30, and the torque tube 16 form a fluid conduit through which fluid and debris generated during the atherectomy procedure may be withdrawn from the patient. The funnel 48 is preferably fabricated from a flexible material such as PET.

To simplify construction of the present invention, it has been found to be particularly practical to fabricate the distal hub 28 and blades 38a–38d as a single piece. In cases where a single piece construction is used for the distal hub 28 and the blades 38a–38d, it may be appreciated that the proximal hub 30 may be formed by bonding or otherwise attaching the proximal ends 42 of each blade 38a–38d to the distal end 46 of the torque tube 16.

OPERATION

Figure 4:
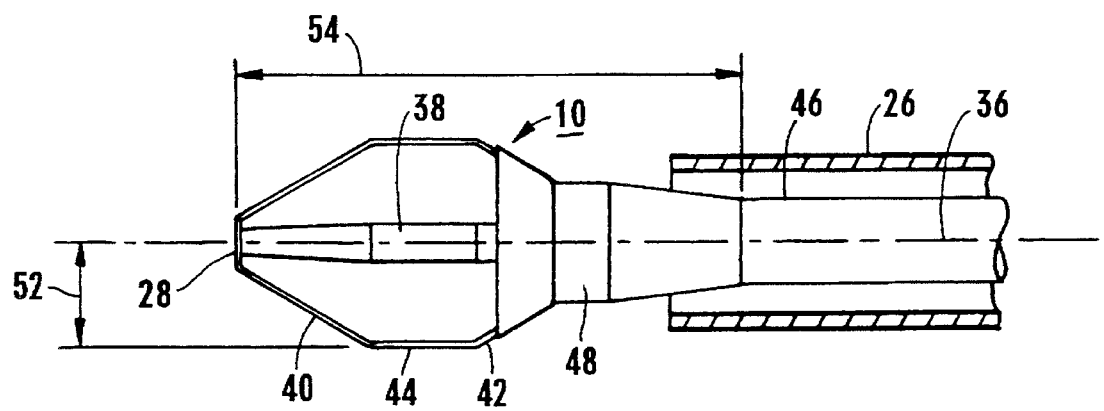
FIG. 4 is a side elevational view of the cutter of the present invention shown in an expanded configuration and a cross sectional view of the guide catheter of the present invention.

As previously discussed, the cutter 10 is designed to be insertable into the guide catheter 26. This functionality is best visualized by reference to FIGS. 4 and 5. In FIG. 4, the cutter 10 is shown to be substantially in the expanded, or cutting, configuration. It may be seen that the cutter 10, and more specifically the blades 38a and 38b of the cutter 10, describe a cutting radius 52. Additionally, it may be seen that the cutter 10 has a corresponding length 54. It may be appreciated that different dimensions may be chosen for both cutting radius 52 and length 54. In practice, however, a value of two millimeters for the cutting radius 52 is particularly appropriate and will result in the desired value of twelve French (or four millimeters) for the overall diameter for the cutter 10.

Figure 5:
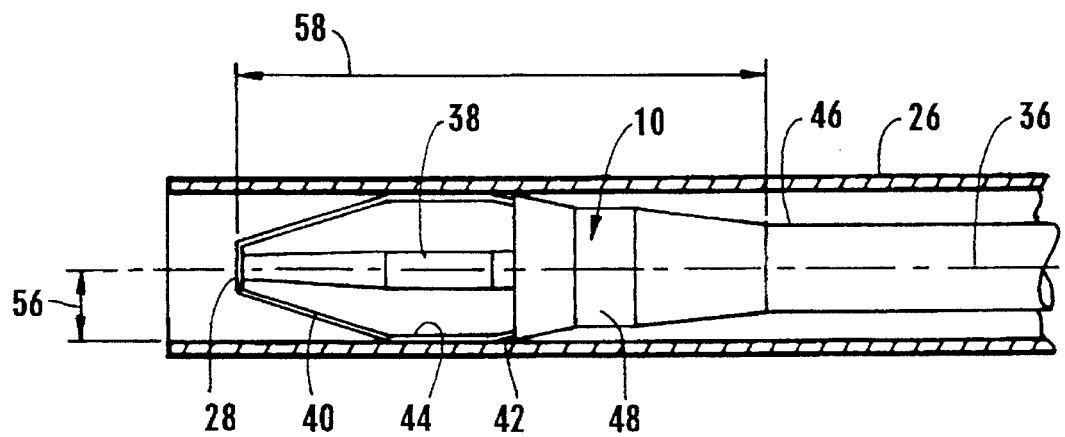
FIG. 5 is a side elevational view of the cutter of the present invention shown in a compressed configuration positioned inside of the guide catheter of the present invention with the guide catheter shown in cross section.

Referring now to FIG. 5, it can be seen that the cutter 10 has been inserted into the guide catheter 26. Additionally, it can be seen that the insertion of the cutter 10 into the guide catheter 26 has caused the cutter 10 to adopt a compressed configuration. The compressed configuration is characterized by a compressed radius 56 and a length 58. In comparison with the cutter 10 shown in FIG. 4, it may be seen that compressed radius 56 is smaller than cutting radius 52. The decrease from cutting radius 52 to compressed radius 56 has necessarily resulted in the increase from length 54 to length 58. The increase from length 54 to length 58 is, of course, due to the blades 38a and 38b which flatten and lengthen as they are compressed during insertion of the cutter 10 into the guide catheter 26. The compressed configuration is also characterize by an equivalent compression of the funnel 48 which flexibly adapts to the configuration of the cutter 10 and prevents the funnel 48 from interfering with the guide catheter 26 as the cutter 10 is inserted into the guide catheter 26.

Once the cutter 10 is inserted into the guide catheter 26, the guide wire 14 is threaded through the aperture 32 and aperture 34 and passed through the torque tube 16. The cutter 10, still positioned within the guide catheter 26, is then advanced along the guide wire 14 until it has reached a location adjacent to the stenosis 24 in the artery 22. Force is then applied to the torque tube 16 to advance the cutter 10 out of the guide catheter 26. As the cutter 10 emerges from the guide catheter 26, the blades 36 expand and the cutter adopts the cutting configuration. Alternatively, the torque tube 16 may be fitted with a retractable sheath which may be withdrawn to expose the cutter. Additionally, it may be seen that exposure of the cutter 10, has allowed the funnel 48 to expand to adapt to the cutting configuration of the cutter 10.

With the cutter 10 in the cutting configuration, the control unit 18 is used to apply the vacuum source 20 to the torque tube 16. The control unit 18 is also used to apply torque to the torque tube 16 to cause the cutter 10 to rotate. The rotating cutter 10 is then advanced into the stenosis 24. As the cutter 10 contacts the stenosis 24, the plaque that comprises the stenosis is forcibly cut away from the artery 22. The vacuum source 20 pulls the severed plaque through the funnel 48, the aperture 34 formed in the proximal hub 30, the torque tube 16 and safely out of the artery 22. The presence of the funnel 48 provides a partial seal which reduces the tendency for severed plaque and other debris to slip past the cutter 10 before the plaque may be removed through the funnel 48.

As the stenosis 24 is cleared, the cutter 10 may be advanced to clear another stenosis. Alternatively, the control unit 18 may be used to discontinue rotation of the cutter 10 and application of the vacuum source 20. Once the cutter 10 has ceased rotating, force may once again be applied to the torque tube 16 to pull the cutter 10 back into the guide catheter 26. The cutter 10 and guide catheter 26 may then be removed from the artery 22.

While the particular expandable and compressible atherectomy cutter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. An atherectomy cutter which comprises:

a rotatable torque tube having a lumen, said torque tube having a distal end;

a proximal hub mounted at said distal end of said torque tube for rotation therewith;

a distal hub positioned distally from said proximal hub at a predetermined separation therefrom;

a plurality of resilient blades, each said blade having a distal end connected to said distal hub and a proximal end connected to said proximal hub, said blades defining a cutting radius, said cutting radius being resiliently compressible with a corresponding increase in said predetermined separation between said proximal hub and said distal hub; and a flexible conically-shaped funnel tapered with an increasing cross-section in a distal direction and formed with an interior surface, said funnel extending distally from said distal end of said torque tube and attached thereto in fluid communication with said lumen of said torque tube at least a portion of each said blade being positioned within said funnel and against said interior surface.

2. A cutter as recited in claim 1 wherein said blades and said distal hub are formed as a single piece.

3. A cutter as recited in claim 1 wherein said blades are fabricated from stainless steel.

4. A cutter as recited in claim 1 wherein said distal hub is formed with an aperture, said aperture dimensioned to allow said cutter to be positioned over a guide wire.

5. A cutter as recited in claim 1 wherein said funnel flexible adapts to the dimensions of said blades.

6. A cutter as recited in claim 1 wherein said funnel is formed from PET.

7. A method for excising plaque from the artery of a patient which comprises the steps of:

providing an atherectomy cutter which comprises a rotatable torque tube having a lumen, said torque tube having a distal end, a proximal hub mounted at said distal end of said torque tube for rotation therewith, a distal hub positioned distally from said proximal hub at a predetermined separation therefrom, a plurality of resilient blades, each said blade having a distal end connected to said distal hub and a proximal end connected to said proximal hub, said blades defining a cutting radius, said cutting radius being resiliently compressible with a corresponding increase in said predetermined separation between said proximal hub and said distal hub, and a flexible conically-shaped funnel tapered with an increasing cross-section in a distal direction and formed with an interior surface, said funnel extending distally from said distal end of said torque tube and attached thereto in fluid communication with said lumen of said torque tube at least a portion of each said blade being positioned within said funnel and against said interior surface;

providing a guide catheter formed with a lumen;

inserting said cutter into said lumen of said guide catheter by compressible causing said blades to adopt said reduced radius;

inserting said cutter and said guide catheter into the artery of a patient and positioning said cutter adjacent to the plaque to be excised;

advancing said cutter out of said guide catheter to allow said blades to adopt said cutting radius; and rotating and advancing said cutter into said artery to excise said plaque.

8. A method as described in claim 7 further comprising the steps of:

prepositioning a guide wire in said artery of said patient; and advancing said atherectomy cutter over said guide wire into said artery.

9. A method as described in claim 7 further comprising the steps of:

providing a vacuum source; and connecting said vacuum source to said torque tube to withdrawn fluid and debris through said funnel and said torque tube from said artery of said patient as said plaque is excised.

10. A method as described in claim 7 further comprising the steps of:

retracting said cutter into said guide catheter; and removing said cutter and said guide catheter from said artery of said patient.

11. An atherectomy cutter which comprises:

a rotatable torque tube having a lumen;

a proximal hub mounted on said torque tube for rotation therewith;

a distal hub positioned distally from said proximal hub at a predetermined separation;

a plurality of resilient blades, each said blade having a distal end attached to said distal hub, and a proximal end attached to said proximal hub, said blades shaped to describe a predetermined cutting radius, said blades resiliently compressible to selectively adopt a reduced radius; and a flexible conically-shaped funnel formed with an interior surface, said funnel attached at said distal end of said torque tube in fluid communication with said lumen of said torque tube, said funnel extending distally from said distal end of said torque tube and expanding radially in a distal direction with at least a portion of each said blade being positioned within said funnel and against said interior surface.

12. A cutter as recited in claim 11 wherein said blades and said distal hub are formed as a single piece.

13. A cutter as recited in claim 11 wherein said distal hub is formed with an aperture, said aperture dimensioned to allow said cutter to be positioned over a guide wire.

14. A cutter as recited in claim 11 wherein said funnel flexible adapts to the dimensions of said blades.

15. A cutter as recited in claim 11 wherein said funnel is formed from PET.

16. A cutter as recited in claim 11 wherein said blades are fabricated from stainless steel.

17. An atherectomy cutter for use with a guide catheter which comprises:

a rotatable torque tube having a lumen, said torque tube having a distal end;

cutting means attached to said distal end of said torque tube for rotation therewith, said cutting means resiliently compressible between a cutting configuration for cutting plague from an artery to a compressed configuration for passage of said cutter through said guide catheter; and a flexible conically-shaped funnel formed with an interior surface, said funnel attached at said distal end of said torque tube in fluid communication with said lumen of said torque tube, said funnel extending distally from said distal end of said torque tube and expanding radially in a distal direction with said cutting means partially positioned within said funnel and against said interior surface.

* * * * *